United States Patent [19]

Ballantine et al.

[11] Patent Number: 4,749,808

[45] Date of Patent: * Jun. 7, 1988

[54] PROTON-CATALYSED REACTIONS IN WHICH WATER IS NOT A STOICHIOMETRIC REACTANT CATALYSED BY METAL CATION EXCHANGED LAYERED CLAYS

[75] Inventors: James A. Ballantine, Swansea; John H. Purnell, Gower, both of Wales; John M. Thomas, Cambridge, England

[73] Assignee: British Petroleum Company p.l.c., London, England

[*] Notice: The portion of the term of this patent subsequent to Apr. 3, 2001 has been disclaimed.

[21] Appl. No.: 878,385

[22] Filed: Jun. 18, 1986

Related U.S. Application Data

[60] Continuation of Ser. No. 639,696, Aug. 13, 1984, abandoned, which is a division of Ser. No. 416,387, Sep. 9, 1982, Pat. No. 4,499,319, which is a continuation-in-part of Ser. No. 218,551, Dec. 22, 1980, abandoned.

[30] Foreign Application Priority Data

| Dec. 22, 1979 [GB] | United Kingdom | 7944315 |
| May 17, 1980 [GB] | United Kingdom | 8016384 |
| Jul. 5, 1980 [GB] | United Kingdom | 8022101 |
| Aug. 9, 1980 [GB] | United Kingdom | 8026028 |

[51] Int. Cl.$^4$ .................. C07C 67/27; C07C 67/04
[52] U.S. Cl. .................. 560/247; 560/240; 560/243; 560/245
[58] Field of Search ............ 560/247, 240, 243, 245

[56] References Cited

U.S. PATENT DOCUMENTS

| 3,578,609 | 5/1971 | Haag et al. | 560/247 |
| 4,440,958 | 4/1984 | Gregory et al. | 560/247 |
| 4,593,135 | 6/1986 | Gregory | 560/247 |

FOREIGN PATENT DOCUMENTS

| 0031687 | 7/1981 | European Pat. Off. | 560/247 |
| 3105399 | 10/1982 | Fed. Rep. of Germany | 560/247 |
| 49-100016 | 9/1974 | Japan | 560/247 |
| 905854 | 9/1962 | United Kingdom | 560/247 |

*Primary Examiner*—Nicky Chan
*Attorney, Agent, or Firm*—Brooks, Haidt, Haffner & Delahunty

[57] ABSTRACT

The invention relates to the use of metal cation-exchangeable layered clays in organic reactions which are catalysed by protons in which intercalated water is not a stoichiometric reactant. Such organic reactions include the production of esters by the reaction of an olefin or an olefin oxide with a carboxylic acid, the production of ethers by reaction of an alcohol with an olefin or an olefin oxide, the production of ethers by the reaction of a primary or secondary aliphatic alcohol or an olefin oxide, the production of bis-sec-alkyl ethers from alkenes, the production of alkyl aromatic compounds by the reaction of an aromatic hydrocarbon with an olefin or alcohol and the production of alcohols by the hydration of olefins.

15 Claims, No Drawings

PROTON-CATALYSED REACTIONS IN WHICH WATER IS NOT A STOICHIOMETRIC REACTANT CATALYSED BY METAL CATION EXCHANGED LAYERED CLAYS

This application is a continuation of application Ser. No. 639,696 filed Aug. 13, 1984, now abandoned, which is a divisional of application Ser. No. 416,387 filed on Sept. 9, 1982, now U.S. Pat. No. 4,499,319, which is a continuation-in-part of application Ser. No. 218,551 filed on Dec. 22, 1980, now abandoned.

The present invention relates generally to proton-catalysed organic reactions in which intercalated water is not one of the stoichiometric reactants and in particular to the use of cation-exchangeable layered clays in which the exchangeable cation is a metal cation as catalysts in such reactions.

Many different types of organic reaction are catalysed by protons or, to give them another name, hydrogen ions. Typical of such reactions are olefin hydration in which the product is an alcohol, esterification of an alcohol with an acid in which the product is an ester and the decomposition of organic hydroperoxides, e.g. cumene hydroperoxide, in which the products are phenol and acetone. Generally the protons are provided by the dissociation of a strong mineral acid or a strong organic acid. Thus sulphuric acid and para-toluene sulphonic acid have been used extensively as catalysts in the industrial production of esters, and phosphoric acid, usually supported on silica, is a catalyst commonly employed in the commercial production of ethanol. Comparatively recently hydrogen ion-exchanged resins have been employed as catalysts in, for example, the production of alkanols.

In the Journal of Physical Chemistry, Volume 44, No. 2, February 1940, pp 180 to 184, there is disclosed the preparation of an acid bentonite by electrodialyzing a 4 percent suspension of Wyoming bentonite in a cell of the Mattson type until the catholyte liquor is no longer alkaline followed by ion-exchange of the acid bentonite with an aqueous solution of a metal salt to produce a metal cation-exhanged bentonite and the use of a metal cation-exchanged bentonite so-prepared as catalyst in the decomposition of hydrogen peroxide.

U.S. Pat. No. 4,278,820 describes a process for producing a monoalkylene glycol monoether by reacting an alkylene oxide having 2 to 4 carbon atoms with an aliphatic alcohol having 1 to 4 carbon atoms in which the improvement comprises performing the reaction in the presence of a solid catalyst resulting from the exchanging of exchangeable cations of a clay composed mainly of montmorillonite with at least one cation selected from the group consisting of aluminium, chromium, manganese, iron, tin and thorium. In the Examples accompanying U.S. Pat. No. 4,278,820 one of the steps in the catalyst production procedure involves calcination at 500° C. for 2 hours.

Thereafter in the Journal of Catalysis 58, 238–252 (1979) Adams et al disclosed that metal cation-exchanged water-intercalated clays such as metal cation-exchanged water-intercalated montmorillonites will convert alkenes to the corresponding bis-sec-alkyl ethers. In some circumstances 100% conversion of usable intercalated water to ether was achieved but it was not possible to obtain further amounts of bis-sec-alkyl ethers by the addition of more water to the reaction.

We have now found that cation-exchangeable layered clays in which the exchangeable cation is a metal cation catalyse organic reactions which are catalysed by protons in which intercalated water is not one of the stoichiometric reactants. An example of such a reaction is the direct reaction of olefins with acids to make esters.

Accordingly the present invention provides a process for carrying out a proton-catalysed organic reaction in which intercalated water is not one of the stoichiometric reactants characterised in that there is used as catalyst a cation-exchangeable layered clay in which the exchangeable cation is a metal cation.

A layered clay within the context of the present specification is a clay having a lamellar structure with interlamellar spaces disposed between the lamellar layers. Typical of such clays is montmorillonite which has an idealised stoichiometric composition corresponding to $Na_{0.67}[Al_{3.33}Mg_{0.67}](Si_8)O_{20}(OH)_4$. Structurally it comprises a central octrahedrally coordinated layer containing aluminium and magnesium in the form of their oxides and hydroxides sandwiched between two layers containing tetrahedrally coordinated silicon essentially in the form of its oxide. Normally in nature cations are present to compensate for the charge imbalance caused by isomorphous substitution of $Mg^{2+}$ for $Al^{3+}$ in the octahedral layer, and/or $Al^{3+}$ or other ions for $Si^{4+}$ in the tetrahedral layers. The octahedral and tetrahedral regions are tightly bound together to form a lamellar layer. The space between these lamellar layers, i.e. the interlamellar space, in natural clays is normally occupied by exchangeable $Ca^{2+}$ or $Na^+$ ions. The distance between the interlamellar layers can be substantially increased by absorption of a variety of polar molecules such as water, ethylene glycol, amines etc., which enter the interlamellar space and in doing so push apart the lamellar layers. The interlamellar spaces tend to collapse when the molecules occupying the space are removed, for example by heating the clay at a high temperature. Both natural and synthetic clays having a layered structure are well known and may be used in the process of the invention after exchange of the interlamellar metal cations normally associated therewith with other metal cations. Besides montmorillonites such as bentonite and Fullers Earths, other types of suitable clays include hectorites, beidellites, vermiculites and nontronite. A preferred clay is a bentonite, such as Wyoming bentonite.

As hereinbefore described the clays in their natural state normally contain exchangeable sodium or calcium ions in the interlamellar space. Such clays have some catalytic activity in the process of the present invention. In order to bestow increased catalytic activity on the clay it is necessary to exchange some or all of the exchangeable metal cations with cations of one or more other suitable metals. Examples of suitable metals include chromium, aluminium, cobalt, nickel, iron, copper and vanadium, of which chromium and aluminium are preferred.

Ion-exchange itself is a technique well known in the art. Although any of the variants of that technique may be used in the preparation of catalysts useful in the process of the present invention the metal cation-exchanged clay is preferably prepared by exchanging the sodium or calcium or other exchangeable cations in a natural clay with an aqueous solution of a metal salt rather than by exchanging with ammonium ions from an aqueous solution of an ammonium compound to form the ammonium ion-exchanged clay, followed by calcination of the ammonium ion-exchanged clay to form the hydrogen ion-exchanged clay and subsequent exchange with an aqueous solution of a metal salt to produce the metal cation-exchanged clay. This preference arises from the desirability of avoiding excessively high temperatures, such as those used during calcination, because the use of such high temperatures tends to collapse the lamellar structure of the clay and leads to inactive catalysts. Suitably exchange may be effected at or near ambient temperature, preferably from about 0° C. to about 35° C. The exchange period will depend to some extent on the temperature. Typically, at ambient temperature the exchange period may be in the range from ½ hour to 3 days.

Techniques for separating the metal cation-exchanged clay from the ion-exchange media and excess ions are well known. Any suitable solid/liquid separation procedure can be used. Decantation or centrifugation are two preferred methods for solid/liquid separation.

After exchange the metal cation-exchanged clay is preferably washed until all extraneous metal cations are removed and dried, suitably at a temperature which does not result in collapse of the interlamellar space. Generally, drying temperatures in the range 20° to 100° C. are suitable. It is preferred to activate the metal cation-exchanged clay before use as a catalyst by heating in air at a temperature which does not lead to collapse of the interlamellar structure, typically up to about 200° C., preferably from 80° to 200° C. The catalyst may suitably be combined with other compounds, for example silica, in order to aid pellet or particle stability.

Cation-exchangeable layered clays in which the exchangeable cation is a metal cation may be used as catalysts in all organic reactions catalysed by protons in which intercalated water is not one of the stoichiometric reactants. Advantages arising from their use are that they can be readily separated from the reaction mixture which renders them useful in continuous processes, and they are less corrosive than the strong acids conventionally employed. We have found the clays to be particularly useful catalysts in certain specific organic reactions, such as the production of esters by the reaction of an olefin or an olefin oxide with a carboxylic acid, the production of ethers by reaction of an alcohol and an olefin or an olefin oxide, the production of an ether by the reaction of a primary or secondary aliphatic alcohol or an olefin oxide, the production of an alkyl aromatic compound by the reaction of an aromatic hydrocarbon and an olefin or an alcohol and the production of an alcohol by the hydration of an olefin.

In a particular aspect therefore the present invention provides a process for the production of an ester which process comprises reacting either an olefin or an olefin oxide with a carboxylic acid in the presence as catalyst of a cation-exchangeable layered clay in which the exchangeable cation is a metal cation under reaction conditions which result in the formation of an ester.

With regard to the olefin or olefin oxide reactant any suitable olefin or olefin oxide may be employed. Suitable olefins include ethylene, propylene, butenes, pentenes and hexenes, diolefins such as butadiene and cyclic olefins such as cyclohexene. Mixtures of olefins such as those commonly encountered in refinery streams such as those derived from the steam cracking of hydrocarbons, e.g. cat-cracked spirit, may also be used if so desired. Suitable olefin oxides include ethylene oxide and propylene oxide. The amount of the olefin or olefin oxide employed may be greater or less than the stoichiometric amount required to react completely with the acid.

Both aromatic and aliphatic carboxylic acids may be used. Suitable aliphatic acids include formic, acetic, propionic and butyric acids. Of the aromatic acids phthalic acids, especially ortho-phthalic acid, may be employed. Mixtures of acids may also be used.

Preferably the olefin is ethylene, the carboxylic acid is acetic acid and the ester produced is ethyl acetate. Alternatively, ethylene glycol diacetate and 2-hydroxyethyl acetate can be obtained from the reaction of ethylene oxide and acetic acid.

A preferred metal cation-exchanged layered clay for use in this process is a chromium or aluminium ion-exchanged Wyoming bentonite.

The process may be carried out in the liquid phase or in the vapour phase, preferably in the liquid phase. Reaction conditions which result in the formation of esters will depend on whether the process is carried out in the liquid or the vapour phase and to some extent on the nature of the reactants.

In the liquid phase the pressure is suitably any pressure which maintains a liquid phase at the reaction temperature. In the case of olefins and olefin oxides with suitably high boiling points, e.g. hexene-1, the reaction may for example be conveniently carried out at the reflux temperature of the reactants and under atmospheric pressure, or at higher temperatures and pressure if so desired. The temperature may suitably be in the range 20° to 300° C. In the case of ethylene, for example, the temperature may be in the range 100° to 300° C., preferably 150° to 250° C. Generally, using olefin oxides lower temperatures within the aforesaid range may be employed. In the case of propylene oxide, for example, the temperature may suitably be in the range 20° to 150° C., preferably 50° to 150° C. Solvents may be employed if desired. Suitable solvents include hydrocarbons, e.g. alkanes such as hexane and octane. In the vapour phase the conditions must be chosen so that the reactants do not liquefy; for example in the production of ethyl acetate from ethylene and acetic acid, the acetic acid must be fed at atmospheric or slightly higher pressure otherwise it would liquefy at higher pressures. Generally, any temperature which does not result in breakdown of the layered structure of the clay may be employed. In the case of the reaction of ethylene and acetic acid, for example, the temperature may suitably be in the range 120° to 200° C., preferably 140° to 180° C. For the reaction of ethylene and acetic acid the residence time which is defined as:

$$\frac{\text{Volume of catalyst in mls}}{\text{Vapour flow rate (in mls/sec at } NTP\text{)}}$$

may suitably be in the range 10 to 60 secs, preferably 20 to 40 secs.

The process may be carried out batchwise or continuously, preferably continuously. The batchwise liquid phase production of ethyl acetate, for example, may conveniently be carried out by charging acetic acid and catalyst to an autoclave, pressurising the autoclave with ethylene, heating the autoclave to the desired reaction temperature and maintaining the autoclave at the reaction temperature. The reaction time should not be unduly protracted otherwise the selectivity for the conversion of acetic acid to ethyl acetate may be adversely affected. Thus at an approximately 2:1 molar ratio of ethylene to acetic acid, an initial ethylene pressure of 55 bar and a temperature of 200° C., the reaction time should preferably not exceed 5 hours. At the completion of the reaction the catalyst may be separated from the product, suitably by filtration, centrifugation or decantation and the reaction product worked up in known manner to recover ethyl acetate therefrom. The catalyst may thereafter be re-used in a further batch reaction with or without intervening treatment.

The invention also provides a process for the production of an ether which process comprises reacting at ambient or an elevated temperature and in the presence of a cation-exchangeable layered clay in which the exchangeable cation is a metal cation an alcohol with either an olefin having the structure:

or an olefin oxide having the structure:

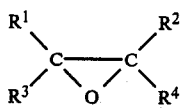

wherein $R^1$, $R^2$, $R^3$ and $R^4$ are independently H, alkyl or aryl or are bonded together to form a ring.

Suitably the alcohol may be an aliphatic, cycloaliphatic or aromatic alcohol, which may be mono-, di- or polyhydric. Examples of suitable aliphatic alcohols include methanol, ethanol, propanols, butanols, pentanols and hexanols. An example of a suitable cyclo-aliphatic alcohol is cyclohexanol and an example of an aryl alcohol is phenol. Diols, such as ethylene glycol and propylene glycol and polyols, such as glycerol may be used. Mixtures of alcohols and/or diols and/or polyols may also be employed if desired.

With regard to the olefin or olefin oxide any suitable olefin or olefin oxide may be employed. Suitable olefins include ethylene, propylene, butenes, pentenes and hexenes, diolefins such as butadiene and cyclic olefins such as cyclohexene. Preferably the olefin is a $C_3$ to $C_6$ olefin. Mixtures of olefins, such as those commonly encountered in refinery streams, such as those derived from the steam cracking of hydrocarbons, e.g. cat cracked spirit, may also be used if so desired. Suitable olefin oxides include ethylene oxide and propylene oxide. The amount of olefin or olefin oxide employed may be greater or less than the stoichiometric amount required to react completely with the alcohol. Generally, using an olefin oxide, it is preferred to employ a stoichiometric excess of the alcohol in order to maximise the yield of the desired ether. Preferably the excess of alcohol to olefin oxide is from 5:1 to 15:1 (molar).

A preferred catalyst for use in this process is an aluminium or chromium ion-exchanged Wyoming bentonite. In preferred embodiments of the invention mono-, di- and tri-ethylene glycol mono alkyl ethers, where alkyl=methyl, ethyl or butyl, are produced by reacting ethylene oxide with methanol, ethanol or butanol respectively; mono-, di- and tri-propylene glycol mono alkyl ethers are produced by reacting propylene oxide with an alkanol and 2-methoxybutane is produced by reacting methanol with linear butenes.

The process may be carried out in the liquid phase or in the vapour phase, preferably in the liquid phase. Reaction conditions which result in the formation of an ether will depend on whether the process is carried out in the liquid or the vapour phase and to some extent on the nature of the reactants.

In the liquid phase the pressure is suitably any pressure which maintains a liquid phase at the reaction temperature. In the case of olefins with suitably high boiling points, the reaction may for example be conveniently carried out at the reflux temperature of the reactants and under atmospheric pressure, or at higher temperatures and pressures if so desired. Generally, for olefins the temperature may be between 80° and 300° C., preferably 150° to 250° C. Using olefin oxides it is preferred to employ generally lower temperatures, which may suitably be in the range 15° to 200° C., preferably from 25° to 150° C. The particular temperature employed within the aforesaid ranges will depend upon the nature of the olefin or olefin oxide. Solvents may be employed if so desired. Suitable solvents include hydrocarbons, e.g. alkanes such as hexane and octane. A preferred solvent is sulpholane.

The process may be carried out batchwise or continuously preferably continuously.

The invention also provides a process for the production of an ether by reacting at elevated temperature a primary or secondary aliphatic alcohol or a polyol in the presence of a metal cation-exchangeable layered clay in which the exchangeable cation is a metal cation.

With regard to the primary aliphatic alcohol reactant suitable alcohols include methanol, ethanol, propan-1-ol, butan-1-ol, pentan-1-ol, hexan-1-ol, heptan-1-ol and octan-1-ol. The principal ether in the product resulting from the reaction of a primary aliphatic alcohol in the presence of the layered clays is the corresponding 1,1-ether, though the corresponding 1,2-ether, may also be formed. Alkenes and alkene dimers may also be formed. Generally the proportion of alkene in the product increases as the carbon number of the reactant alcohol increases.

With regard to the secondary aliphatic alcohol reactant suitable alcohols include straight-chain alcohols such as propan-2-ol, butan-2-ol, pentan-2-ol, pentan-3-ol hexan-2-ol and hexan-3-ol and cyclohexanol, of which propan-2-ol and butan-2-ol are preferred. The ethers predominating in the product resulting from the reaction of alkan-2-ols and alkan-3-ols are the 2,2- and 3,3-ethers respectively. Alkenes and alkene dimers are also formed.

The reactant may also be a polyol such as an alkylene glycol. A suitable alkylene glycol is ethylene glycol which produces a mixture of dioxan, and ethylene glycol oligomers (di-ethylene glycol, etc). A preferred alkylene glycol is diethylene glycol which produces dioxan in high conversions in the presence of the layered clay. Additionally mixtures of alcohols and/or polyols may be used if so desired.

The elevated temperature may suitably be in the range 100° to 300° C., preferably from 150° to 225° C.

The process may be carried out in the liquid phase or the vapour phase, preferably in the liquid phase.

The invention also provides a process for the production of an ether by reacting an olefin oxide at elevated temperature in the presence as catalyst of a metal cation-exchangeable layered clay in which the exchangeable cation is a metal cation.

Suitable olefin oxides which may be used include ethylene oxide and propylene oxide. Thus, for example, reaction of ethylene oxide yields 1,4-dioxan and 2-methyl-1,3-dioxan and the products from the reaction of propylene oxide include 2,5-dimethyl-1,3-dioxan. Other epoxides yield cyclic ethers, but alpha, beta-unsaturated aldehydes may also be formed. The proportion of unsaturated aldehyde generally tends to increase with the carbon number of the epoxide.

The process may be carried out in the liquid phase or the vapour phase, preferably in the liquid phase. The temperature may suitably be in the range 15° to 200° C., preferably 80° to 200° C.

The invention also provides a process for the production of an alkyl aromatic compound by reacting at elevated temperature an aromatic hydrocarbon with an alkylating agent selected from olefins and $C_2$ or higher alcohols in the presence as catalyst of a metal cation-exchangeable layered clay in which the exchangeable cation is a metal cation.

The aromatic hydrocarbon may suitably be benzene, naphthalene or other polycyclic aromatic hydrocarbon. Aromatic hydrocarbons substituted by alkyl or other functional groups, such as for example, hydroxyl, alkoxy and hydroxyalkyl, may also be employed. Preferably the aromatic hydrocarbon is benzene or toluene. Mixtures of aromatic hydrocarbons may also be employed if so desired.

The olefin may suitably be a mono-olefin or a diolefin. Suitable mono-olefins include ethylene, propylene and butylenes, though higher olefins, such as for example propylene tetramer, may be employed. Mixtures of olefins may also be employed. A suitable diolefin is butadiene.

Examples of suitable $C_2$ or higher alcohols which may be employed include ethanol, n-propanol and iso-propanol.

In a preferred embodiment of this aspect of the invention benzene is reacted with propylene to produce iso-propylbenzene (cumene). In another preferred embodiment benzene is reacted with ethylene to produce ethylbenzene. In yet another preferred embodiment phenol is reacted with an alkylating agent to produce alkylphenols.

Reaction of an aromatic hydrocarbon with an alkylating agent may suitably be effected in the liquid phase or in the vapour phase, preferably in the liquid phase. Typically, reaction of an aromatic hydrocarbon with an olefin may be carried out in the liquid phase at a temperature up to 400° C., preferably in the range 150° to 300° C. and at an elevated pressure sufficient to maintain a liquid phase.

The process may be operated batchwise or continuously, preferably continuously.

Typically, under continuous flow conditions, benzene may be alkylated with isopropylene at a temperature in the range from 100° to 400° C., preferably from 150° to 300° C., at atmospheric or elevated pressure, preferably from 20 to 50 bar. The molar ratio of benzene to propylene may be in the range from about 0.1:1 to 100:1, preferably from 3:1 to 20:1. The metal cation-exchanged clay may be any suitable size or shape as to ensure good contact with the reactants. Suitably, particles or pellets may be employed. The ratio of catalyst volume to liquid feed volume flow rate (residence time) may for example be up to 5 hours and is preferably in the range from 1 minute to 2 hours. The conditions may be permutated either to maximise desirable products such as cumene or diisopropylbenzene or to minimise any unwanted by-products.

Typically, phenol may be alkylated at a temperature in the range from 50° to 300° C., preferably from 100° to 200° C., at atmospheric or elevated pressure. For example, phenol may be alkylated with high-boiling olefins, e.g. hexene-1, at atmospheric pressure and at about 120° C. in a stirred glass vessel fitted with a reflux condenser. Using lower boiling olefins, e.g. ethylene and propylene, as the alkylating agent, elevated pressures may be employed to facilitate contact between the phenol and olefin reactants. Alternatively, there may be used other methods of mixing whereby, the use of elevated pressure can be avoided, for example by bubbling the olefin through molten phenol containing the catalyst.

The invention also provides a process for the production of an alcohol which process comprises reacting an olefin with water at elevated temperature and pressure in the presence as catalyst of a metal cation-exchangeable layered clay in which the exchangeable cation is a metal cation.

Suitably the olefin may be a lower olefin such as ethylene, propylene or a butylene, though higher olefins and mixtures of olefins may be employed if desired. Mixtures of olefins also comprise hydrocarbon fractions which contain substantial amounts, e.g. about 25 to about 90% by weight of olefins. In a preferred embodiment the olefin is ethylene and the product produced by reaction with water in the presence of the catalyst is ethanol. In another preferred embodiment sec-butanol is produced by reacting linear butenes with water.

The process may be operated batchwise or continuously, preferably continuously.

In conducting the process of the invention the olefin and water or steam may suitably be passed over the catalyst together at a reactant feed rate corresponding to a space velocity based on liquid reactant in the range of about 0.25 to 10 volumes of liquid feed per volume of catalyst per hour, i.e. about 0.25 to 10 L.H.S.V. The water to olefin mole ratio may be in the range of about 1:1 to 500:1, preferably 5:1 to 400:1.

The total pressure in the reactor may range from about 50 psig to about 1500 psig and the temperature may be in the range from 50° to 400° C. The specific temperature chosen depends on the reactivity of the olefin. Thus, propylene and the butenes are considerably more reactive than ethylene, and for the former olefins a temperature in the range of about 100° to about 240° C. is suitable. For ethylene the temperature may suitably be in the range from about 200° to 400° C. Since low temperatures are associated with high values of the equilibrium constant for alcohol formation, it is desirable to hydrate at the lowest temperature compatible with a reasonable rate of conversion.

The liquid phase reaction may be carried out in the presence of a solvent. A suitable solvent, for example, is ethyl carbitol.

The process may suitably be conducted in what is conventionally known as a "trickle bed" reactor, with at least a portion of the water in the liquid phase. Alternatively, the process may be operated in the gas phase.

The invention will now be illustrated by reference to the following Examples.

All analytical results were determined using gas chromatography and the identity of the products was confirmed by comparison with authentic materials, mass spectroscopy or nuclear magnetic resonance spectroscopy. Generally, the quantitative analyses are expressed by weight but in some cases flame ionisation gas chromatograph areas are used to express the results.

PREPARATION OF METAL CATION-EXCHANGED LAYERED CLAY

A. Aluminium and chromium-exchanged bentonite

Finely divided sodium bentonite was cation exchanged with 0.5M aqueous solutions of appropriate salts at room temperature for a period of approximately 24 hours (the chromium salt employed was $Cr_2(SO_4)_3$; the aluminium salt employed was $Al_2(SO_4)_3.16H_2O$). The solutions were mechanically stirred during the first 2 hours of a period of 24 hours, after which the solid was washed repeatedly with deionised water until the excess cations had been removed. Surplus liquid was removed from the solid using a teat-pipette prior to drying in a vacuum oven at 60° C. When the clay was visibly dry it was ground until it passed 140 BSS mesh sieve. The cation-exchanged clay was then equilibrated over granular anhydrous calcium chloride in a dessicator for a minimum period of 24 hours.

B. Aluminium-exchanged bentonite

Wyoming bentonite powder (100 g) was added to a solution of aluminium sulphate $[Al_2(SO_4)_3.16H_2O]$ (250 g) in distilled water (1.5 l) and left overnight. The clay was centrifuged, mixed with a further 1.5 liters of water and recentrifuged. This was repeated a second time to remove all extraneous ions. Finally the aluminium-exchanged clay was oven dried at 80° C.

C. Cupric ion-exchanged bentonite

The procedure outlined in B above was repeated except that the aluminium sulphate was replaced by cupric sulphate.

D. Ferric ion-exchanged bentonite

The procedure outlined in B above was repeated except that the aluminium sulphate was replaced by ferric nitrate.

E. Chromic ion-exchanged bentonite

The procedure outlined in B above was repeated except that the aluminium sulphate was replaced by chromic nitrate.

Production of Esters by Reaction of an Olefin or an Olefin Oxide with a Carboxylic Acid in the Liquid Phase

EXAMPLE 1

$Cr^{3+}$-exchanged bentonite (0.5 g) prepared as described in A above, hex-1-ene (5 ml) and acetic acid (1.5 ml) were placed in a standard steel reactor of capacity 20 ml. The reactor was closed by a screw cap provided with an O-ring seal and immersed up to the screw cap in a silicone oil bath which was maintained at 200° C. After 4 hours the reactor was removed from the bath, cooled and its contents analysed. The results in terms of the weight percentage of individual products in the product mixture (rounded to the nearest whole number) are given in Table 1.

EXAMPLE 2

Example 1 was repeated except that the $Cr^{3+}$-exchanged bentonite was replaced by $Al^{3+}$-exchanged bentonite prepared as described in A above and the acetic acid was replaced by propionic acid.

EXAMPLE 3

Example 1 was repeated except that the $Cr^{3+}$-exchanged bentonite was replaced by $Al^{3+}$-exchanged bentonite prepared as described in A above and the acetic acid was replaced by isobutyric acid.

EXAMPLE 4

Example 1 was repeated except that hex-1-ene was replaced by hept-1-ene.

EXAMPLE 5

Example 1 was repeated except that hex-1-ene was replaced by oct-1-ene.

EXAMPLE 6

Example 1 was repeated except that $Cr^{3+}$-exchanged bentonite was replaced by $Al^{3+}$-exchanged bentonite prepared as described in A above and hex-1-ene was replaced by 4-methylpent-1-ene.

EXAMPLE 7

Example 1 was repeated except that $Cr^{3+}$-exchanged bentonite was replaced by $Al^{3+}$-exchanged bentonite prepared as described in A above and hex-1-ene was replaced by hex-2-ene.

The results of Examples 1 to 7 are given in Table 1.

EXAMPLE 8

Acetic acid (80 g) and $Al^{3+}$-exchanged Wyoming Bentonite catalyst (10 g, 9.4% wt Al) prepared as described in B above were charged to a 100 ml stirred autoclave. The autoclave was charged with ethylene to a pressure of 55 bar (ethylene:acetic acid mole ratio 2:1). The temperature of the autoclave was raised to 250° C. and maintained at this value for 2.5 hr.

At the end of the reaction period the autoclave was cooled, vented and the product analysed. The yield of ethyl acetate was 25% and the selectivity to ethyl acetate was greater than 99%, both yield and selectivity being based on acetic acid.

EXAMPLE 9

Example 8 was repeated except that the autoclave was pressurised to 150 bar with ethylene and the temperature was reduced to 200° C. The yield of ethyl acetate was 35% and the selectivity greater than 99%.

EXAMPLE 10

Example 8 was repeated except that the temperature was reduced to 200° C. The yield of ethyl acetate was 18% at a selectivity greater than 99%.

EXAMPLE 11

Example 10 was repeated except that the catalyst was activated before use by heating in air at 200° C.

The yield of ethyl acetate was 28% compared to 18% in Example 10.

EXAMPLE 12

Example 11 was repeated except that the catalyst heat treatment was carried out above 300° C. This treatment led to substantial catalyst deactivation. The yield of ethyl acetate was about 4% compared with 18% in Example 10.

EXAMPLE 13

Aluminium-exchanged bentonite prepared as described in B above (10 g) and acetic acid (80 g) were sealed in a 100 ml stirred autoclave which was charged with 40 bar pressure of ethylene. The autoclave was heated at 200° C. for 2.5 hours giving a maximum pressure of 55 bar. After cooling and venting, the liquid products were analysed. The results are shown in Table 1A.

EXAMPLE 14

Example 13 was repeated except that the cupric ion-exchanged bentonite prepared as described in C above (10 g) was used as catalyst in place of aluminium-exchanged bentonite.

EXAMPLE 15

Example 13 was repeated except that the ferric ion-exchanged bentonite prepared as described in D above was used as catalyst in place of aluminium-exchanged bentonite.

EXAMPLE 16

Example 13 was repeated except that the chromic ion-exchanged bentonite prepared as described in E above was used as catalyst in place of aluminium-exchanged bentonite.

EXAMPLE 17

Example 13 was repeated except that before use as a catalyst the aluminium-exchanged bentonite was calcined at 300° C. for 16 hours.

The results of Examples 14 to 18 are given in Table 1A.

EXAMPLE 18

Ethylene oxide (5 ml), acetic acid (2.5 ml) and aluminium-exchanged bentonite (0.5 g) prepared as described in A above were placed in a steel reactor of capacity 20 ml. The reactor was sealed with a screw cap and heated to 100° C. After 60 minutes the reactor was cooled and the contents analysed. The product contained 1,4-dioxan (35%), ethylene glycol diacetate (17%) 2-hydroxyethylacetate (11%), 2-methyl-1,3,-dioxan (7%) and but-2-en-1-al (3%) together with unchanged reactants and some unidentified minor components.

Production of Ethers by Reacting an Alcohol with an Olefin or an Olefin Oxide

EXAMPLE 19

The procedure described in Example 1 was followed except that the $Cr^{3+}$-exchanged bentonite was replaced by $Al^{3+}$-exchanged bentonite prepared as described in A above and hex-1-ene/acetic acid were replaced by a 50:50 v/v mixture (5 ml) of hexan-1-ol and hex-1-ene. The analysis of the product mixture gave:

|  | wt % of product mixture |
|---|---|
| Hexenes | 53 |
| Hexanol | 8 |
| 1,1-ether | 9 |
| 1,2, and 1,3-ethers | 4 |

EXAMPLE 20

5 g of the dry aluminium-exchanged bentonite prepared as described in B above, hex-1-ene (25 g) and methanol (19 g) were sealed in a Baskerville 100 ml stainless steel autoclave fitted with a stirrer. The autoclave was heated at 200° C. for 2.5 hours, and then cooled. The liquid products (32.0 g, 73% weight recovered) were recovered and shown to contain 2-methoxyhexane (10.2%) and dimethyl ether (4.9%) as the two major new products. The product percentages are based on peak areas shown in a flame ionisation gas chromatograph. The gaseous products were not examined.

EXAMPLE 21

5 g of the dry aluminium-exchanged bentonite prepared as described in B above and methanol (19 g) were cooled to −20° C. in the bottom-half of a Baskerville 100 ml stainless steel autoclave. But-1-ene (ca 20 ml of condensed liquid in a cardice cold trap) was added and the autoclave sealed. The autoclave was flushed with nitrogen and stirred at 200° C. for 2.5 hours, and allowed to cool. The liquid products (7 g, 10% weight recovered) were recovered and shown to contain 2-methoxybutane (34.7%), and $C_4$ dimers (56.2%) as the two major new peaks. The product percentages are based on peak areas shown on a flame ionisation gas chromatograph. The gaseous products were not examined.

EXAMPLE 22

Aluminium-exchanged bentonite prepared as described in B above (3.75 g) and ethylene glycol (30 g) were sealed in a 100 ml stirred autoclave which was then charged with liquid propene (40 ml). The autoclave was heated at 175° C. for 2.5 hours giving a maximum pressure of 35 bar. After cooling and venting, analysis of the liquid product showed:
Isopropyl cellosolve: 8.8% w/w
Dioxan: 4.1% w/w
Digol: 1.6% w/w
Propanol: 0.2% w/w

EXAMPLE 23

Example 22 was repeated except that but-1-ene was added in place of the propene. The results are shown in Table 2.

EXAMPLE 24

Example 23 was repeated except that the amount of ethylene glycol was reduced from 30 g to 20 g and sulpholane (20 g) was added as solvent. The results are shown in Table 2.

EXAMPLE 25

Example 24 was repeated except that chromic ion-exchanged bentonite prepared as described in E above was used in place of the aluminium-exchanged bentonite. The results are shown in Table 2.

EXAMPLE 26

Aluminium-exchanged bentonite (1.5 g) prepared as described in B above was added to ethanol (100 g; 2.17 mole) in a 500 cm² flask equipped with a dry ice/acetone condenser and the mixture was stirred at room temperature. Propylene oxide (34.2 g; 0.23 mole) was added dropwise. Analysis of the products after a few minutes showed almost quantitative conversion of the propylene oxide to mono-propylene glycol mono-ethyl ether and di-propylene glycol mono-ethyl ether (about 9:1 ratio by weight).

EXAMPLE 27

Example 26 was repeated except that the propylene oxide was replaced by ethylene oxide (14 g; 0.23 mole) and the amount of ethanol was increased to 123 g (2.8 mole). Almost quantitative conversion of the ethylene oxide to mono-ethylene glycol mono-ethyl ether and di-ethylene glycol mono-ethyl ether (about 9:1 ratio by weight) was achieved.

EXAMPLE 28

Ethylene oxide (2.5 ml) ethanol (2.5 ml) and aluminium-exchanged bentonite (0.5 g) prepared as described in A above were placed in a steel reactor of capacity 20 ml. The reactor was sealed with a screw cap and heated to 110° C. After 4 hours the reactor was cooled and the contents analysed. The product contained diethyl ether (2%), ethylene glycol diethyl ether (1%), and diethylene glycol mono-ethylether (21%) together with unchanged reactants and some unidentified minor components.

Production of Ethers by Reaction of a Primary or Secondary Aliphatic Alcohol or a Polyol

EXAMPLE 29

$Al^{3+}$-exchanged bentonite prepared as described in A above (0.5 g) and butan-1-ol were placed in a standard steel reactor of capacity 20 ml. The reactor was closed by a screw cap provided with an O-ring seal and immersed up to the screw cap in a silicone oil bath maintained at 200° C. After 4 hours the reactor was removed from the bath, cooled and its contents analysed.

EXAMPLE 30

Example 29 was repeated except that butan-1-ol was replaced by pentan-1-ol.

EXAMPLE 31

Example 29 was repeated except that butan-1-ol was replaced by hexan-1-ol.

EXAMPLE 32

Example 29 was repeated except that butan-1-ol was replaced by heptan-1-ol.

EXAMPLE 33

Example 29 was repeated except that butan-1-ol was replaced by octan-1-ol.

EXAMPLE 34

Example 29 was repeated except that butan-1-ol was replaced by 3-methylbutan-1-ol.

EXAMPLE 35

Example 29 was repeated except that butan-1-ol was replaced by 3-methylbutan-1-ol.

EXAMPLE 36

Example 29 was repeated except that butan-1-ol was replaced by butan-2-ol.

EXAMPLE 37

Example 29 was repeated except that butan-1-ol was replaced by butan-2-ol.

EXAMPLE 38

Example 29 was repeated except that butan-1-ol was replaced by pentan-2-ol.

EXAMPLE 39

Example 29 was repeated except that butan-1-ol was replaced by hexan-2-ol.

EXAMPLE 40

Example 29 was repeated except that butan-1-ol was replaced by 2-methylbutan-2-ol. This example is included to illustrate the fact that tertiary alkanols yield only alkene and alkene dimers. Identical results have been obtained from 2-methylpropan-2-ol, 2-methylpentan-2-ol and 3-methylpentan-3-ol.

The results of Examples 30 to 40 in terms of the wt. % of individual products in the product mixture (rounded to the nearest whole number) are given in Table 3.

EXAMPLE 41

Example 29 was repeated except that butan-1-ol was replaced by diethylene glycol.

Analysis of the product showed:

|  | wt % reaction mixture |
| --- | --- |
| Unreacted glycol | 57 |
| Dioxan | 20 |
| Ethylene glycol | 9 |
| Triethylene glycol | 14 |
| Others | 1 |

The Production of Ethers by Reaction of an Olefin Oxide

EXAMPLE 42

Ethylene oxide (5 ml) and aluminium-exchanged bentonite (0.5 g) prepared as described in A above were placed in a steel reactor of capacity 20 ml. The reactor was sealed with a screw cap and heated to 110° C. After 6 hours the reactor was cooled and the contents analysed. The product contained 1,4-dioxan (68%) and 2-methyl-1,3-dioxan (16%) together with unchanged reactants and some unidentified minor components.

EXAMPLE 43

Propylene oxide (5 ml) and aluminium-exchanged bentonite (0.5 g) prepared as described in A above were placed in a steel reactor of capacity 20 ml. The reactor was sealed with a screw cap and heated to 200° C. After 8 hours the reactor was cooled and the contents analysed. The product contained dimethyl-1,4-dioxan (4%), 2-methyl-2-pentanol (35%) and dimethyl-1,3-dioxans (16%) together with unchanged reactant and some unidentified minor components.

The Production of an Alcohol by Reacting an Olefin with Water

EXAMPLE 44

Aluminium-exchanged bentonite prepared as described in B above (3.75 g) and water (40 g) were sealed in a 100 ml stirred reactor which was then charged with liquid butene-1 (40 ml). The autoclave was heated to 200° C. for 2.5 hours giving a maximum pressure of 65 bar. After cooling and venting the liquid products were analysed. The yield of butan-2-ol in the product was 1.20 g, corresponding to a conversion of butene-1 to butan-2-ol of 3.2%.

EXAMPLE 45

Example 44 was repeated except that chromic ion-exchanged bentonite prepared as described in E above (3.75 g) was used instead of the aluminium-exchanged bentonite. The yield of butan-2-ol in the product was 0.54 g, corresponding to a conversion of butene-1 to butan-2-ol of 1.5%.

EXAMPLE 46

A reactor in a continuous plant was charged with a mixture of the aluminium-exchanged bentonite particles prepared as described in B above (20 ml) and a pelleted inert diluent (20 ml) and the reactor pressure was raised to 45 bar with ethylene. The pressure was maintained by a slow bleed of ethylene out of the pressurised system. Water was pumped into the reactor at a rate of 40 ml liquid per hour. The temperature of the reactor was increased gradually from 100° C. to 400° C. and the liquid products were examined for ethanol. In the reactor temperature range 250° to 330° C. the products contained 5% wt ethanol in the range 330° to 370° C., 4.5% wt ethanol was obtained. No other products were observed.

The Production of an Alkyl Aromatic Compound by Reacting an Aromatic Hydrocarbon with an Alkylating Agent

EXAMPLE 47

In a glass tube reactor was placed aluminium-exchanged bentonite particles (20 ml) prepared as described in B above through which was passed a mixture of benzene and ethylene in a molar ratio of 8:1. The residence time was 10 seconds, the temperature of the reactor was 386° C. and the pressure was atmospheric. An ethylene conversion to ethyl benzene of 6.1% was obtained. The weight ratio of ethyl benzene to diethyl benzenes was about 32:1 The selectivity of both benzene and ethylene to ethyl benzene was approximately 95%.

EXAMPLE 48

Aluminium exchanged bentonite (0.5 g) prepared as described in A above, benzene (2.5 ml), and hex-1-ene (2.5 ml) were placed in a steel reactor of capacity 20 ml. The reactor was sealed with a screw cap and heated to 200° C. After 4 hours the reactor was cooled and the contents analysed by gas liquid chromatography. The product contained mono-hexyl benzenes (42%), di-hexyl benzenes (18%), unreacted benzene (22%), hexenes (15%) and minor components (3%).

EXAMPLE 49

Example 48 was repeated except that the benzene was replaced by toluene (2.5 ml). The product contained mono-hexyl toluenes (28%), unreacted toluene (48%), hexenes (22%) and minor components (2%).

EXAMPLE 50

Example 48 was repeated except that the hex-1-ene was replaced by cyclohexene (2.5 ml). The product contained mono-cyclohexyl benzene (23%), unreacted benzene (27%), cyclohexene (46%), and minor components (4%).

EXAMPLE 51

Example 48 was repeated using benzene (4 ml) and ethanol (1 ml) in place of the benzene and hex-1-ene reactants. The liquid products contained ethyl benzene (0.5%), unreacted benzene (84%), ethanol (0.5%) and di-ethyl ether (15%). Water and ethylene were not determined quantitatively.

EXAMPLE 52

Example 48 was repeated using benzene (4 ml) and isopropanol (1 ml) in place of the benzene and hex-1-ene reactants. The product contained cumene (43%), di-isopropyl benzenes (8%), tri-isopropyl benzenes (2%), isopropanol (4%) and unreacted benzene (43%) excluding propylene and water which were not determined quantitatively.

EXAMPLE 53

Example 48 was repeated using phenol (2 g) and hex-1-ene (3 ml) in place of the benzene and hex-1-ene reactants and the reaction was carried out at 220° C. The products contained mono-hexyl phenols (63%), di-hexyl phenols (12%), unreacted phenol (11%), hexenes (12%), hexyl phenyl ethers (1%) and minor components (1%).

TABLE 1

| Example | Catalyst | Alkene | Acid | Unreacted alkene | Unreacted acid | Total esters | Alkene dimers |
|---|---|---|---|---|---|---|---|
| | | | | wt. % in product mixture | | | |
| 1 | $Cr^{3+}$-bentonite | Hex-1-ene | acetic | 41 | 36 | 16 | 7 |
| 2 | $Al^{3+}$-bentonite | Hex-1-ene | propionic | 31 | 33 | 11 | 25 |
| 3 | $Al^{3+}$-bentonite | Hex-1-ene | isobutyric | 45 | 38 | 6 | 11 |
| 4 | $Cr^{3+}$-bentonite | Hept-1-ene | acetic | 47 | 37 | 11 | 5 |
| 5 | $Cr^{3+}$-bentonite | Oct-1-ene | acetic | 60 | 28 | 12 | 0 |
| 6 | $Al^{3+}$-bentonite | 4MePent-1-ene | acetic | 49 | 22 | 12 | 17 |
| 7 | $Al^{3+}$-bentonite | Hex-2-ene | acetic | 50 | 20 | 21 | 7 |

TABLE 1A

| Example | Catalyst | Alkene | Acid | % weight ethyl acetate in liquid product | Selectivity, acetic acid to ethyl acetate (%) |
|---|---|---|---|---|---|
| 13 | $Al^{3+}$-bentonite | ethylene | acetic | 18 | 99+ |
| 14 | $Cu^{2+}$-bentonite | ethylene | acetic | 10 | 90 |
| 15 | $Fe^{3+}$-bentonite | ethylene | acetic | 15 | 99+ |
| 16 | $Cr^{3+}$-bentonite | ethylene | acetic | 18 | 99+ |
| 17 | $Al^{3+}$-bentonite | ethylene | acetic | 2.5 | 99 |

TABLE 2

| | % w/w in liquid product | | |
|---|---|---|---|
| Example | sec-Butyl cellosolve | Dioxan | Digol |
| 23 | 14.3 | 0.5 | 4.2 |

TABLE 2-continued

| | % w/w in liquid product | | |
|---|---|---|---|
| Example | sec-Butyl cellosolve | Dioxan | Digol |
| 24* | 26.7 | 0 | 1.6 |
| 25* | 25.1 | 6.4 | 5.3 |

*product analysis excludes sulpholane solvent

TABLE 3

| | | Weight % of reaction product | | | | |
|---|---|---|---|---|---|---|
| Example | Alkanol | Unreacted alkanol | 2,2 dialkyl ether | 1,1 dialkyl ether | 1,2 dialkyl ether | Alkenes | Alkene dimers |
| 29 | Butan-1-ol | 39 | — | 51 | 4 | 6* | 1 |
| 30 | Pentan-1-ol | 42 | — | 38 | 4 | 11 | 6 |
| 31 | Hexan-1-ol | 30 | — | 45 | 4 | 16 | 4 |
| 32 | Heptan-1-ol | 42 | — | 34 | 2 | 15 | 6 |
| 33 | Octan-1-ol | 38 | — | 36 | — | 20 | 6 |
| 34 | 3-Mebutan-1-ol | 50 | — | 35 | — | 4 | 12 |
| 35 | 3-Mepentan-1-ol | 44 | — | 25 | — | 15 | 16 |
| 36 | Propan-2-ol | 49 | 47 | — | — | 3* | 1 |
| 37 | Butan-2-ol** | 35 | 32 | — | — | 25* | 1 |
| 38 | Pentan-2-ol | 9 | 6 | — | — | 85 | 1 |
| 39 | Hexan-2-ol | 3 | 1 | — | — | 95 | 2 |
| 40 | 2-Mebutan-2-ol | 3 | — | — | — | 90 | 7 |

*Due to loss of gaseous alkenes on sampling these figures are minimised, hence all others in the relevant line of the Table are maxima.
**The 7% deficit in this analysis is butan-2-one which appears to be an impurity in the reactant.

We claim:

1. In a process for the production of an ester by reacting at elevated temperature an olefin or an olefin oxide with a carboxylic acid in the presence of a catalyst, the improvement which comprises employing as a catalyst a cation-exchangeable layered clay in which some or all of the exchangeable cations have been exchanged with cations of at least one other suitable metal selected from the group consisting of chromium, aluminium, cobalt, nickel, iron, copper and vanadium.

2. A process as claimed in claim 1 wherein some or all of the exchangeable cations have been exchanged with aluminium cations.

3. A process as claimed in claim 1 wherein some or all of the exchangeable cations have been exchanged with chromium cations.

4. A process as claimed in claim 1 wherein the exchangeable cations are exchanged by cation-exchanging the cation-exchangeable layered clay with an aqueous solution of a metal salt, separating the metal cation-exchanged layered clay from the aqueous solution of the metal salt, washing until all the extraneous metal cations are removed and drying at a temperature which preserves the lamellar structure.

5. A process as claimed in claim 4 wherein cation-exchange is effected at a temperature in the range 0° to 35° C.

6. A process as claimed in claim 1 wherein the olefin or olefin oxide is selected from the group consisting of ethylene, hex-1-ene, hept-1-ene, oct-1-ene, 4-methyl-pent-1-ene, hex-2-ene and ethylene oxide and the carboxylic acid is selected from acetic acid, propionic acid and isobutyric acid.

7. A process as claimed in claim 1 wherein the olefin is ethylene, the carboxylic acid is acetic acid and the ester is ethyl acetate.

8. A process as claimed in claim 1 wherein the cation-exchangeable layered clay is a montmorillonite.

9. A process as claimed in claim 1 wherein the olefin is contacted with the carboxylic acid in the liquid phase.

10. A process according to claim 1 wherein the olefin is contacted with the carboxylic acid at a temperature in the range from 100° to 300° C.

11. A process as claimed in claim 1 wherein the olefin is contacted with the carboxylic acid in the vapour phase.

12. A process as claimed in claim 2 wherein the olefin is contacted with the carboxylic acid at a temperature in the range from 120° to 180° C. and a residence time in the range from 10 to 60 seconds.

13. A process as claimed in claim 1, wherein the catalyst is a cation-exchangeable dioctahedral layered clay selected from the group consisting of montmorillonites, beidellites, vermiculites and nontronite.

14. A process as claimed in claim 1, wherein the cation-exchangeable layered clay is bentonite.

15. A process as claimed in claim 1, wherein the reaction temperature is in the range of from 200° C. to 300° C.

* * * * *